US006534286B1

(12) United States Patent
Li et al.

(10) Patent No.: US 6,534,286 B1
(45) Date of Patent: Mar. 18, 2003

(54) PROTEIN PRODUCTION IN AUREOBASIDIUM PULLULANS

(75) Inventors: Xin-Liang Li, Athens, GA (US); Lars G. Ljungdahl, Athens, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 09/595,344

(22) Filed: Jun. 15, 2000

(51) Int. Cl.$^7$ ............................ C12P 21/06; C12N 9/00; C12N 1/20; C12N 15/00; C12N 5/00
(52) U.S. Cl. ...................... 435/69.1; 435/183; 435/200; 435/252.1; 435/252.3; 435/254.1; 435/320.1; 435/325; 435/69.8; 435/69.9; 435/254.2; 435/254.11; 536/23.1; 536/23.2; 536/241
(58) Field of Search ............................... 435/69.1, 183, 435/200, 252.1, 252.3, 254.1, 320.1; 536/23.2

(56) References Cited

U.S. PATENT DOCUMENTS 5,591,619 A    1/1997    Li et al. ...................... 435/201

FOREIGN PATENT DOCUMENTS

| WO | WO 00/09717 | 2/2000 | ........... C12N/15/76 |
| WO | WO 00/32798 | 6/2000 | ........... C12N/15/80 |

OTHER PUBLICATIONS

Ohta, K. et al., "Purification and Characterization of an Acidophilic Xylanase from *Aureobasidium pullulans* var. *melanigenum* and Sequence Analysis of the Encoding Gene" (Oct. 2001) J. of Bioscience and Bioengineering 92(3):262–270.
Gen Bank Accession No. AF169630, Vanden Wymelenberg, A. (Aug. 31, 1999), Aureobasidium pullulans xylanase (*xynA*) gene.
Leathers et al. (1984) "Overproduction and Regulation of Xylanase in *Aureobasidium pullulans* and *Crytococcus albidus*" Biotechnology and Bioengineering Symposium 14:225–240.

Leathers et al. (1986) "Induction and Glucose Repression of Xylanse from a Color Variant Strain of *Aureobasidium pullulans*" *Biotechnology Letters* 8(12):867–872.
Li, Wei et al. (1997) "Assay of β–glucuronidase Activity in intact transformed *Aureobasidium pullulans* spores" *Fungal Genetics Newsletter* 44:29–32.
Li, Xin–Liang et al. (1993) "Purification and Characterization of a New Xylanase (APX–II) from the Fungus *Aureobasidium pullulans* Y–2311–1" *Applied and Environmental Microbiology* 59(10):3212–3218.
Li, Xin–Liang et al. (1994) "Cloning, Sequencing, and Regulation of a Xylanase Gene from the Fungus *Aureobasidium pullulans* Y–2311–1" *Applied and Environmental Microbiology* 60(9):3160–3166.
Li, Xin–Liang et al. (1996) "Expression of *Aureobasidium pullulans xynA* in, and Secretion of the Xylanase from, *Saccharomyces cerevisiae*" *Applied and Environmental Microbiology* 62(1):209–213.
Vanden Wymelenberg et al. (1999) "Regulated expression of green fluorescent protein under the control of *Aureobasidium pullulans* xylanase gene *xynA*" *FEMS Microbiology Letters* 181:205–209.
Genbank Accession No. APU10298; released May 25, 1995.
GenBank Accession No: AF169630, dated Aug. 31, 1999.*

\* cited by examiner

*Primary Examiner*—Rebecca E. Prouty
*Assistant Examiner*—Manjunath N. Rao
(74) *Attorney, Agent, or Firm*—Greenlee Winner and Sullivan, PC

(57) ABSTRACT

The present disclosure provides methods and DNA molecules for the synthesis of heterologous proteins in the fungus *Aureobasidium pullulans* either intracellularly or with secretion out of the cells using a regulated xylanase promoter and for secreted protein synthesis, a signal sequence. Further described are kits containing host cells for recombinant protein production, a vector containing an XynA transcription regulatory sequence, and instructions for using the vector to transform the host cells.

34 Claims, 1 Drawing Sheet

SEQUENCE LISTING

<160> NUMBER OF SEQ ID NOS: 21

<210> SEQ ID NO 1
<211> LENGTH: 1945
<212> TYPE: DNA
<213> ORGANISM: Aureobasidium pullulans

<400> SEQUENCE: 1

```
aagcttgttg aacaagcctt gatttccgca caatagtgcg tttcaggcgg agccgaggtc      60
aggctcgggc gctcgaattg tggagtgctg aagacatcta ctactcattt atgagaatgc     120
ttcatctctt ccgcgttctc gcaaggattt atattaagcc aggaggtcag ctaatctgta     180
tctgcatacc cgcatatcac tcgagtgggt acacgacaga atctcgaact ggcgaattgc     240
gaaagcatcg cgtggtgttc ctgcagcgaa caaatagaa taaagttaca caccacgacc     300
cgaccccaca tcctttatag cggctaaggt gtaagtttca cgcctgcatg gaagcatgca     360
ccagacgata tagagtatat gctacaatat aagctctcgg ccgtacaacg ttcttcgtat     420
agccatactt cgagtatacc aatgacacgt ccggataaaa gagtcagagc catccaaaca     480
cagcatttcg cgtggagcat atccaagcga ggtgtcgtgc ttgtctcgtc acactttaat     540
ctgcttcgca ttcgatttca ggcgagcaag gatatcccag attccagatc taacaaaatc     600
acggctaaac gatgcctgga taggatatat aaggactacc accttccctc ccatcagcaa     660
ctcattctag cacattcatt caaatccatt cacatccatt caaacaatac ttccaactct     720
cttcaacatg aagttcttcg ccaccattgc tgctctcgtt gtgggagctg ttgctgcccc     780
```

```
agtcgcagag gctgaggctg aggccagcag ccccatgctg gtacgatctc ttcgatgaac     840
cattctattc gagaccatct tgctgatcaa cacaataga tcgaacgtgc cggtcccggt      900
ggcatcaact acgtccagaa ctacaacggc aacctgggcc agttcaccta caatgagaac    960
gctggtacct actccatgta ctggaacaac ggtgtcaatg gcgacttcgt cgttggtctc   1020
ggttggtcaa ccggtgctgc ccgctccatc acctactctt ccaactacca ggccagcggc   1080
ggttcttacc tgtccgtcta cggctggatc aacagccccc aggctgagta ctacattgtc   1140
gagtcttacg gctcgtacaa cccttgcggc gccggtcagt ccggtgtcac tcagctcggc   1200
accgtctgca gcgatggcgc tacctacacc gtctacaccg acactcgtac caaccagccc   1260
tccatcactg gtacttctac cttcaagcag tactggtctg tccgccagac taagcgtact   1320
tccggcacgg tcaccactgg caaccacttt gcttactggg ccaagtacgg ctttggcaac   1380
tcttacaact tccaggtcat gcctgtcgag gcttttctctg gcactggtag cgccagtgtc  1440
accgtctctt aaatgtcgga acaagtggct gaatttggat gttggaaagg aggttgtttg   1500
ggatgcggat gaaacgctga tgaagatatg atgttgatct ggttgtgtcc atttatgcta   1560
gcttgtcatt cgttagcaca aagtaaatgt cagacacctt gctactacca tatgctctcc   1620
atgccctatg aatttcactt ttctgttcag ttgagggttt cggaatttcg gcccagatca   1680
atgcataggg cagaaaaatc tggtgatctt actgccgcaa gttggcagaa ttttcctagc   1740
tcaaggccag actcgatcgt caagctggcc tgacgtcgtc aactagatga attatagtac   1800
ccttcagccc agaaaaatgg tagtctcgcg atcagacgtc ttcagacatt cgaacatgac   1860
atgaatatct acgtcaggac atactgaata aatggtgttc gagtagatca gcctcacgag   1920
tccgagccat aggaatccag aattc                                         1945
```

<210> SEQ ID NO 2
<211> LENGTH: 221
<212> TYPE: PRT
<213> ORGANISM: Aureobasidium pullulans
<220> FEATURE:
<221> NAME/KEY: SIGNAL
<222> LOCATION: (1)..(34)

<400> SEQUENCE: 2

```
Met Lys Phe Phe Ala Thr Ile Ala Ala Leu Val Val Gly Ala Val Ala
  1               5                  10                  15

Ala Pro Val Ala Glu Ala Glu Ala Glu Ala Ser Ser Pro Met Leu Ile
             20                  25                  30

Glu Arg Ala Gly Pro Gly Gly Ile Asn Tyr Val Gln Asn Tyr Asn Gly
         35                  40                  45

Asn Leu Gly Gln Phe Thr Tyr Asn Glu Asn Ala Gly Thr Tyr Ser Met
     50                  55                  60

Tyr Trp Asn Asn Gly Val Asn Gly Asp Phe Val Val Gly Leu Gly Trp
 65                  70                  75                  80

Ser Thr Gly Ala Ala Arg Ser Ile Thr Tyr Ser Ser Asn Tyr Gln Ala
                 85                  90                  95

Ser Gly Gly Ser Tyr Leu Ser Val Tyr Gly Trp Ile Asn Ser Pro Gln
            100                 105                 110

Ala Glu Tyr Tyr Ile Val Glu Ser Tyr Gly Ser Tyr Asn Pro Cys Gly
        115                 120                 125

Ala Gly Gln Ser Gly Val Thr Gln Leu Gly Thr Val Cys Ser Asp Gly
    130                 135                 140
```

```
Ala Thr Tyr Thr Val Tyr Thr Asp Thr Arg Thr Asn Gln Pro Ser Ile
145                 150                 155                 160

Thr Gly Thr Ser Thr Phe Lys Gln Tyr Trp Ser Val Arg Gln Thr Lys
                165                 170                 175

Arg Thr Ser Gly Thr Val Thr Thr Gly Asn His Phe Ala Tyr Trp Ala
            180                 185                 190

Lys Tyr Gly Phe Gly Asn Ser Tyr Asn Phe Gln Val Met Pro Val Glu
        195                 200                 205

Ala Phe Ser Gly Thr Gly Ser Ala Ser Val Thr Val Ser
    210                 215                 220

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 3
actacgtcca gaactacaac g                                         21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 4
acactcagct cggcaccgtc t                                         21

<210> SEQ ID NO 5
<211> LENGTH: 28
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 5
gtagctagca gtcgacagaa gatgatat                                  28

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 6
ctagctagcg gtcggcatct actctatt                                  28

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 7
cccaagctag ttgaacaagc cttg                                      24
```

```
<210> SEQ ID NO 8
<211> LENGTH: 52
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 8
acctctagag cggccgcgga gctccaaagc ttggcacgtt cgatctattg tg        52

<210> SEQ ID NO 9
<211> LENGTH: 53
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 9
acctctagag cggccgcgga gctccaaagc ttcttcatgt tgaagagagt tgg       53

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 10
ggaattctgg attcctatgg c                                          21

<210> SEQ ID NO 11
<211> LENGTH: 37
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 11
gctctagagg tacccgggta aatgtcggaa caagtgg                         37

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 12
cccaagcttt tacgtcctgt agaaacccca                                 30

<210> SEQ ID NO 13
<211> LENGTH: 32
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 13
gctctagatt atgccagtcc agcgtttttg ca                              32
```

<210> SEQ ID NO 14
<211> LENGTH: 32
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 14
tttggagctc cggtactgct tggaatggta gt                              32

<210> SEQ ID NO 15
<211> LENGTH: 33
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 15
cctctagagt tagtttcttg gtgcatcata aga                             33

<210> SEQ ID NO 16
<211> LENGTH: 34
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 16
cgtctagagg taccgggccg catcatgtaa ttag                            34

<210> SEQ ID NO 17
<211> LENGTH: 27
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 17
taccccgggc cgcaaattaa agccttc                                    27

<210> SEQ ID NO 18
<211> LENGTH: 20
<212> TYPE: PRT
<213> ORGANISM: Artificial Sequence
<220> FEATURE:
<223> OTHER INFORMATION: Description of Artificial Sequence:amino acid
      sequence encoded by multiple cloning site of SEQ
      ID NO:19.

<400> SEQUENCE: 18

Ile Glu Arg Ala Lys Leu Trp Ser Ser Ala Ala Ala Leu Gly Val Pro
 1               5                  10                  15

Gly Arg Ile Met
            20

<210> SEQ ID NO 19
<211> LENGTH: 74
<212> TYPE: DNA
<213> ORGANISM: Artificial Sequence
<220> FEATURE:
<223> OTHER INFORMATION: Description of Artificial Sequence:multiple
      cloning site sequence.

-continued

```
<400> SEQUENCE: 19
acaatagatc gaacgtgcca agctttggag ctccgcggcc gctctagagg taccgggccg      60
catcatgtaa ttag                                                        74

<210> SEQ ID NO 20
<211> LENGTH: 17
<212> TYPE: PRT
<213> ORGANISM: Artificial Sequence
<220> FEATURE:
<223> OTHER INFORMATION: Description of Artificial Sequence:amino acid
      sequence encoded by multiple cloning site linker
      sequence of SEQ ID NO:21.

<400> SEQUENCE: 20

Met Lys Leu Trp Ser Ser Ala Ala Ala Leu Gly Val Pro Gly Arg Ile
  1               5                  10                  15

Met

<210> SEQ ID NO 21
<211> LENGTH: 76
<212> TYPE: DNA
<213> ORGANISM: Artificial Sequence
<220> FEATURE:
<223> OTHER INFORMATION: Description of Artificial Sequence:multiple
      cloning site linker sequence.

<400> SEQUENCE: 21
cttccaactc tcttcaacat gaagctttgg agctccgcgg ccgctctaga ggtaccgggc      60
cgcatcatgt aattag                                                      76
```

PROTEIN PRODUCTION IN AUREOBASIDIUM PULLULANS

CROSS REFERENCE TO RELATED APPLICATIONS

Not applicable.

ACKNOWLEDGMENT OF FEDERAL RESEARCH SUPPORT

Not applicable.

BACKGROUND OF THE INVENTION

The field of this invention is the production of recombinant proteins, in particular, using regulated gene expression (the xynA promoter) in *Aureobasidium pullulans*.

The yeast-like fungus *Aureobasidium pullulans* has been isolated from various ecosystems, and different isolates display morphologic diversity. The fungus has been extensively studied for its capability to produce high levels of xylanase and pullulan and for its ubiquitous distribution on plant leaves. *A. pullulans* Y-2311-1has been shown to produce the highest levels of xylanase among several xylanolytic fungi [Leathers, T. D. (1986) *Appl. Environ. Microbiol.* 52:1026–1030; Leathers et al. (1984) *Biotechnol. Bioeng. Symp.* 14:225–250; Leathers et al. (1986) *Biotechnol. Lett.* 8:867–872]. The fungus is able to grow on glucose, xylose, glycerol, or arabinose as carbon source. Plant biomass such as wheat bran, corn fiber and starch (but not pure cellulose) also supports rapid growth of the fungus. Xylan and xylose induce while glucose represses the production of xylanolytic activity. Four xylanases which differ in isoelectric points are produced under inducing conditions, but most of the activity is attributed to two xylanase molecules (20 and 25 kDa) [Leathers, T. D. (1986) supra; Li et al. (1993) *Appl. Environ. Microbiol.* 59:3212–3218], differing in glycosylation, encoded by a single gene (xynA) in the fungal genome [Li and Ljungdahl (1994) *Appl. Environ. Microbiol.* 60:3160–3166; Li and Ljungdahl (1997) U.S. Pat. No. 5,591,619]. The two xylanases account for over 80% by weight of the total extracellular proteins in cultures grown on arabinoxylan-rich or xylose medium. It has been shown that either xylan or xylose induced the transcription of the xylanase gene [Li and Ljungdahl (1994) supra; Vanden Wymelenberg et al. (1999) *FEMS Microbiol. Lett.* 181:205–205]. The genomic xynA was amplified by polymerase chain reaction (PCR), and sequencing analysis revealed that a 59-bp intron was located in the DNA region encoding the signal peptide. The xylanase cDNA has been inserted into a plasmid under the control of a yeast Gal1 promoter and high levels of xylanase were secreted by *Saccharomyces cerevisiae*[Li and Ljungdahl (1996) *Appl. Environ. Microbiol.* 62:209–213; Li and Ljungdahl (1997) supra].

Hemicellulose, second only to cellulose in abundance on earth, comprises xylan as the main constituent. Xylan is a hetero-polymer comprising beta- 1,4-linked xylose units as a backbone and side chains which contain pentose, hexose, and acetyl groups. The pentose (arabinose) is esterified to free and lignin phenolic (feruloyl and p-coumaroyl) groups [Christov and Prior (1993) *Enzyme Microb. Technol.* 15:460–475]. Xylan can be readily converted to xylose and other monomeric sugars through either chemical or enzymatic hydrolysis of agricultural and forestry waste biomass. Enzymatic degradation of hemicelluloses requires the participation of several enzymes including xylanase (EC3.2.1.8), β-xylosidase (EC3.2.1.37), α-L-arabinofuranosidase (EC3.2.1.55), α-glucuronidase (EC3.2.1.1), acetyl xylan esterase (EC3.1.1.6) as well as p-coumaroyl and feruloyl esterases [Borneman et al. (1993) In: Hemicellulose and Hemicellulases, M. P. Coughlan and G. Hazlewood (ed.), Portland Press, Cambridge, UK, pp. 85–102; Christov and Prior (1993) supra]. Due to efficient conversion of agricultural plant residues to xylose and widespread use of xylitol, an alcohol derived from xylose in food products, using xylose as an inducer in large-scale fermentation has become cost effective in comparison to other commonly used inducers for fermentation.

There is a long-felt need in the art for regulatable promoters for use in recombinant protein production, where those promoters are regulated and recombinant proteins can be produced using inexpensive substrates.

SUMMARY OF THE INVENTION

It is an object of the present invention to provide a regulated promoter and a signal peptide (and the amino acid sequence encoding it) as well as methods for using the promoter/signal peptide coding sequence for efficient and economical secreted expression of a protein of interest in a eukaryotic cell, especially a fungal cell, for example, *Aureobasidium pullulans*). The signal peptide of the present invention is the XynA (also called APX-II) signal peptide. In general, proteins secreted from cells are synthesized as precursor molecules containing hydrophobic N-terminal signal peptides. The signal peptides direct transport of the protein to its target membrane and are then cleaved by a peptidase on the membrane, such as the endoplasmic reticulum, when the protein passes through it.

This invention also provides for genomic DNA sequence of the xynA locus of *A. pullulans* and the associated transcription regulatory sequences (and the sequences encoding the XynA signal peptide). The gene encoding both these peptides is termed xynA herein. The DNA sequence of the gene as it occurs in *A. pullulans* is given in Table 1 and in SEQ ID NO:1. The transcription start site is about nucleotide 678, based on the size of the xynA transcript, and the coding sequence for the XynA precursor protein is from nucleotide 788 to 1469, excluding a translation stop codon and excluding the intron from nucleotides 821 to 880. There is an intron which extends from nucleotide 821 to 880 (within the coding sequence for the signal peptide), as shown in Table 1, and in SEQ ID NO:1. The DNA sequence provided herein including the intron is useful for recombinantly expressing a secreted protein via the APX-II signal peptide in Aureobasidium species and other host species capable of splicing out the intron. The xynA regulated promoter without the intron is useful for recombinantly expressing the XynA mature protein in *S. cerevisiae* or other host species which are not capable of splicing out the intron. The regulatable xynA promoter is useful for the regulated expression of an operably linked coding sequence, with high levels of gene expression obtained in the presence of the inducing substrates xylan or xylose, where the medium contains glucose a concentration less than about 0.02% (w/v). The xynA xylan- or xylose-responsiveness transcription regulatory sequence is embodied in the nucleotide sequence as set forth in SEQ ID NO:1, or fragments thereof sufficient to retain xylan- or xylan-responsiveness and promoter activity, preferably fragments corresponding to nucleotides 478 to 678, 378 to 678, 278 to 678, 178 to 678, 78 to 678, 1 to 678, and 1 to 733, all as set forth in SEQ ID NO:1.

The XynA signal peptide of this invention has a sequence as given in SEQ ID NO:2 from amino acid 1 to amino acid 34. The term "APX-II signal sequence" encompasses not only the exact sequence given, but also equivalent sequences which have additions, substitutions or deletions which do not interfere with the function of the signal peptide. The coding region for the XynA signal peptide in a construct 5' to a coding sequence for a protein of interest functions to produce an expression product which is secreted efficiently and with high relative purity in the extracellular medium of a fungus, especially A. pullulans. The skilled worker, following the teachings herein, is enabled to make changes to the signal sequence which do not adversely affect its function and thus is enabled to make a large number of operative embodiments of this signal peptide.

The present invention further provides a method for the regulated expression of a protein of interest in a recombinant cell of the genus Aureobasidium, for example, Aureobasidium pullulans, using the xynA promoter derived from A. pullulans operably linked to DNA encoding the protein of interest. The nucleotide sequence of the preferred embodiment of the xynA promoter is given in SEQ ID NO:1, nucleotides 1 to 733.

Expression of the protein of interest is induced when xylose or xylan is added to culture medium having a glucose concentration less than 0.02% (w/v). Desirably xylose is added to a final concentration from about 0.05% (w/v) to about 5.0% (w/v), advantageously from about 0.5% (w/v) to about 1.25% (w/v), and as exemplified, 1% (w/v) xylose. Where xylan is used, the concentration of xylan in the medium is desirably from about 0.05% to about 5.0% (w/v).

DETAILED DESCRIPTION OF THE INVENTION

Figure 1A:
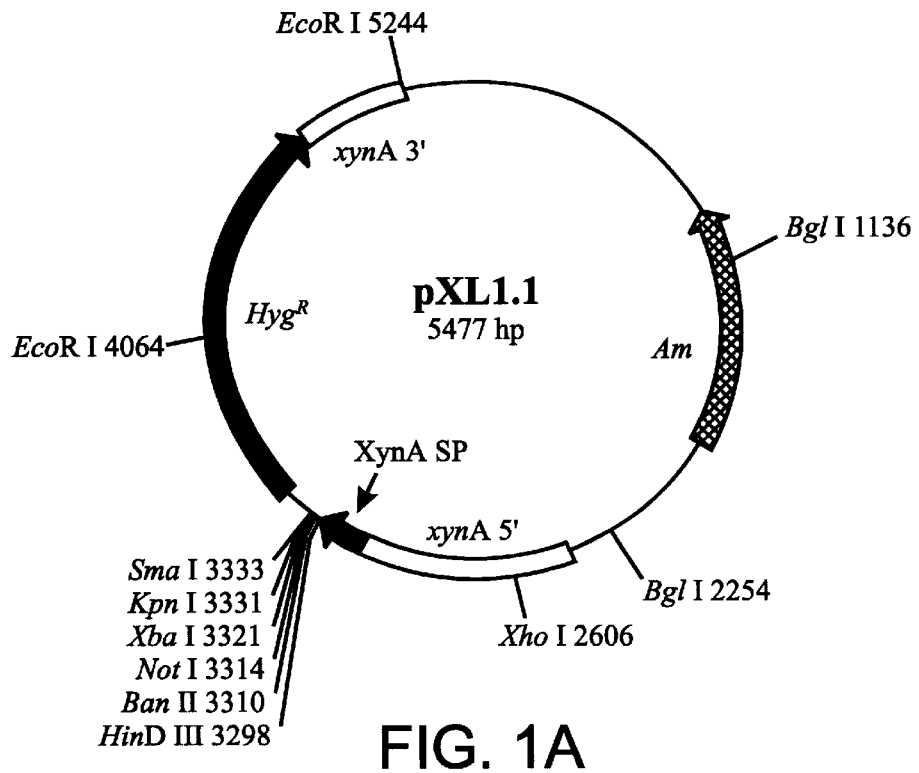
FIGS. 1A–1B: Diagrams and restriction maps of plasmids pXL1.1 and pXL2.1. Symbols: Am, ampicillin resistance gene; hygR, hygromycin B resistance gene; xynA 5', xynA locus 5' sequence; xynA 3', xynA locus 3' sequence; XynA SP, XynA signal peptide sequence. See Table 3 for multiple cloning site (mcs) sequence information.

The amino acids which occur in the various amino acid sequences referred to in the specification have their usual three- and one-letter abbreviations routinely used in the art: A, Ala, Alanine; C, Cys, Cysteine; D, Asp, Aspartic Acid; E, Glu, Glutamic Acid; F, Phe, Phenylalanine; G, Gly, Glycine; H, His, Histidine; I, Ile, Isoleucine; K, Lys, Lysine; L, Leu, Leucine; M, Met, Methionine; N, Asn, Asparagine; P, Pro, Proline; Q, Gln, Glutamine; R, Arg, Arginine; S, Ser, Serine; T, Thr, Threonine; V, Val, Valine; W, Try, Tryptophan; Y, Tyr, Tyrosine.

A protein is considered an isolated protein if it is a protein isolated from a host cell in which it is recombinantly produced. It can be purified or it can simply be free of other proteins and biological materials with which it is associated in nature.

An isolated nucleic acid is a nucleic acid the structure of which is not identical to that of any naturally occurring nucleic acid or to that of any fragment of a naturally occurring genomic nucleic acid spanning more than three separate genes. The term therefore covers, for example, (a) a DNA which has the sequence of part of a naturally occurring genomic DNA molecule but is not flanked by both of the coding or noncoding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in mixtures of (i) DNA molecules, (ii) transformed or transfected cells, and (iii) cell clones, e.g., as these occur in a DNA library such as a cDNA or genomic DNA library.

As used herein expression directed by a particular sequence is the transcription of an associated downstream sequence. If appropriate and desired for the associated sequence, there the term expression also encompasses translation (protein synthesis) of the transcribed RNA. When expression of a sequence of interest is "up-regulated," the expression is increased. With reference to up-regulation of expression of a sequence of interest operably linked to the xynA transcription regulatory sequence, expression is increased in the presence of xylan and/or xylose when the glucose concentration in the medium is less than about 0.02%.

In the present context, a promoter is a DNA region which includes sequences sufficient to cause transcription of an associated (downstream) sequence. The promoter may be regulated, i.e., not constitutively acting to cause transcription of the associated sequence. If inducible, there are sequences present which mediate regulation of expression so that the associated sequence is transcribed only when an inducer molecule is present in the medium in or on which the organism is cultivated. The xynA promoter of the present invention is active only when xylose or xylan is present in the medium. The xynA transcription regulatory sequence is not active when glucose is present at a concentration greater than about 0.02% (w/v). In the present context, a transcription regulatory sequence includes a promoter sequence and the cis-active sequences necessary for regulated expression of an associated sequence in response to environmental signals.

One DNA portion or sequence is downstream of second DNA portion or sequence when it is located 3' of the second sequence. One DNA portion or sequence is upstream of a second DNA portion or sequence when it is located 5' of that sequence.

One DNA molecule or sequence and another are heterologous to another if the two are not derived from the same ultimate natural source. The sequences may be natural sequences, or at least one sequence can be designed by man, as in the case of a multiple cloning site region. The two sequences can be derived from two different species or one sequence can be produced by chemical synthesis provided that the nucleotide sequence of the synthesized portion was not derived from the same organism as the other sequence.

An isolated or substantially pure nucleic acid molecule or polynucleotide is a polynucleotide which is substantially separated from other polynucleotide sequences which naturally accompany a native xynA transcription regulatory sequence. The term embraces a polynucleotide sequence which has been removed from its naturally occurring environment, and includes recombinant or cloned DNA isolates, chemically synthesized analogues and analogues biologically synthesized by heterologous systems.

A polynucleotide is said to encode a polypeptide if, in its native state or when manipulated by methods known to those skilled in the art, it can be transcribed and/or translated to produce the polypeptide or a fragment thereof. The anti-sense strand of such a polynucleotide is also said to encode the sequence.

A nucleotide sequence is operably linked when it is placed into a functional relationship with another nucleotide sequence. For instance, a promoter is operably linked to a coding sequence if the promoter effects its transcription or expression. Generally, operably linked means that the sequences being linked are, contiguous and, where necessary to join two protein coding regions, contiguous and in reading frame. However, it is well known that certain genetic elements, such as enhancers, may be operably linked even at a distance, i.e., even if not contiguous.

The term recombinant polynucleotide refers to a polynucleotide which is made by the combination of two otherwise separated segments of sequence accomplished by the artificial manipulation of isolated segments of polynucleotides by genetic engineering techniques or by chemical synthesis. In so doing one may join together polynucleotide segments of desired functions to generate a desired combination of functions.

Polynucleotide probes include an isolated polynucleotide attached to a label or reporter molecule and may be used to identify and isolate other xynA transcription regulatory sequences, for example, those from other species of Aureobasidium or other strains of *A. pullulans*. Probes comprising synthetic oligonucleotides or other polynucleotides may be derived from naturally occurring or recombinant single or double stranded nucleic acids or be chemically synthesized. Polynucleotide probes may be labeled by any of the methods known in the art, e.g., random hexamer labeling, nick translation, or the Klenow fill-in reaction.

Large amounts of the polynucleotides may be produced by replication in a suitable host cell. Natural or synthetic DNA fragments coding for a protein of interest are incorporated into recombinant polynucleotide constructs, typically DNA constructs, capable of introduction into and replication in a prokaryotic or eukaryotic cell, especially *A. pullulans*, wherein protein expression is desired. In addition to the *A. pullulans* Y-2311-1 strain specifically exemplified herein, others can be used, including but not limited to, *A. pullulans* Y-117 [Li et al. (1997) *Fungal Genetics Newsletter* 44:29–32]; *A. pullulans* R106 [Thornewell et al. (1995) *Gene* 162:105–110]; *A. pullulans* NRRL Y-6220, Y-6754a, Y-12,974, YB-4026 and YB-4588 [Leathers et al. (1988) *J. Indus. Microbiol.* 3:231–239]; and *A. pullulans* CBS 58475 [Dobberstein and Emeis (1989) *Appl. Microbiol. Biotechnol.* 32:262–268]. Usually the construct is suitable for replication in a unicellular host, such as *A. pullulans* or a bacterium, but a multicellular eukaryotic host may also be appropriate, with or without integration within the genome of the host cell. Commonly used prokaryotic hosts include strains of *Escherichia coli*, although other prokaryotes, such as *Bacillus subtilis* or a pseudomonad, may also be used. Eukaryotic host cells include yeast, filamentous fungi, plant, insect, amphibian and avian species, but the regulated expression of a protein of interest a cell of the genus Aureobasidium, especially *A. pullulans*, is preferred. Such factors as ease of manipulation, ability to appropriately glycosylate expressed proteins, degree and control of protein expression, ease of purification of expressed proteins away from cellular contaminants or other factors influence the choice of the host cell.

The polynucleotides may also be produced by chemical synthesis, e.g., by the phosphoramidite method described by Beaucage and Caruthers (1981) *Tetra. Letts.*, 22: 1859–1862 or the triester method according to Matteuci et al. (1981) *J. Am. Chem. Soc.*, 103: 3185, and may be performed on commercial automated oligonucleotide synthesizers. A double-stranded fragment may be obtained from the single stranded product of chemical synthesis either by synthesizing the complementary strand and annealing the strand together under appropriate conditions or by adding the complementary strand using DNA polymerase with an appropriate primer sequence.

DNA constructs prepared for introduction into a prokaryotic or eukaryotic host will typically comprise a replication system (i.e. vector) recognized by the host, including the intended DNA fragment encoding the desired polypeptide, and will preferably also include transcription and translational initiation regulatory sequences operably linked to the polypeptide-encoding segment. Expression systems (expression vectors) may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Signal peptides may also be included where appropriate from secreted polypeptides of the same or related species, which allow the protein to cross and/or lodge in cell membranes or be secreted from the cell.

An appropriate promoter and other necessary vector sequences will be selected so as to be functional in the host. Examples of workable combinations of cell lines and expression vectors are described in Sambrook et al. (1989) vide infra; Ausubel et al. (Eds.) (1995) *Current Protocols in Molecular Biology*, Greene Publishing and Wiley Interscience, New York; and Metzger et al. (1988) *Nature*, 334: 31–36. Many useful vectors for expression in bacteria, yeast, fungal, mammalian, insect, plant or other cells are well known in the art and may be obtained such vendors as Stratagene, New England Biolabs, Promega Biotech, and others. In addition, the construct may be joined to an amplifiable gene (e.g., DHFR) so that multiple copies of the gene may be made. For appropriate enhancer and other expression control sequences, see also *Enhancers and Eukaryotic Gene Expression*, Cold Spring Harbor Press, N.Y. (1983). While such expression vectors may replicate autonomously, they may less preferably replicate by being inserted into the genome of the host cell.

Expression and cloning vectors will likely contain a selectable marker, that is, a gene encoding a protein necessary for the survival or growth of a host cell transformed with the vector. Although such a marker gene may be carried on another polynucleotide sequence co-introduced into the host cell, it is most often contained on the cloning vector. Only those host cells into which the marker gene has been introduced will survive and/or grow under selective conditions. Typical selection genes encode proteins that (a) confer resistance to antibiotics or other toxic substances, e.g., ampicillin, neomycin, methotrexate, etc.; (b) complement auxotrophic deficiencies; or (c) supply critical nutrients not available from complex media. The choice of the proper selectable marker will depend on the host cell; appropriate markers for different hosts are known in the art.

Recombinant host cells, in the present context, are those which have been genetically modified to contain an isolated DNA molecule of the instant invention. The DNA can be introduced by any means known to the art which is appropriate for the particular type of cell, including without limitation, transformation, lipofection or electroporation.

It is recognized by those skilled in the art that the DNA sequences may vary due to the degeneracy of the genetic code and codon usage. All DNA sequences which code for the XynA signal peptide are included in this invention, including DNA sequences as given in SEQ ID:1 having an ATG preceding the coding region for the mature protein, and including DNA sequences with and without the intron identified in Table 1 (and in SEQ ID NO:1).

Additionally, it will be recognized by those skilled in the art that allelic variations may occur in the DNA sequences which will not significantly change activity of the amino acid sequences of the peptides which the DNA sequences encode. All such equivalent DNA sequences are included within the scope of this invention and the definition of the regulated promoter region. The skilled artisan will understand that the sequence of the exemplified xynA regulated promoter sequence and the nucleotide sequence encoding the signal peptide can be used to identify and isolate additional, nonexemplified nucleotide sequences which are functionally equivalent to the sequences given in SEQ ID NO:1, nucleotides 1–733.

Hybridization procedures are useful for identifying polynucleotides with sufficient homology to the subject regulatory sequences to be useful as taught herein. The particular hybridization techniques is not essential to the subject invention. As improvements are made in hybridization techniques, they can be readily applied by one of ordinary skill in the art.

A probe and sample are combined in a hybridization buffer solution and held at an appropriate temperature until annealing occurs. Thereafter, the membrane is washed free of extraneous materials, leaving the sample and bound probe molecules typically detected and quantified by autoradiography and/or liquid scintillation counting. As is well known in the art, if the probe molecule and nucleic acid sample hybridize by forming a strong non-covalent bond between the two molecules, it can be reasonably assumed that the probe and sample are essentially identical, or completely complementary if the annealing and washing steps are carried out under conditions of high stringency. The probe's detectable label provides a means for determining whether hybridization has occurred.

In the use of the oligonucleotides or polynucleotides as probes, the particular probe is labeled with any suitable label known to those skilled in the art, including radioactive and non-radioactive labels. Typical radioactive labels include $^{32}P$, $^{35}S$, or the like. Non-radioactive labels include, for example, ligands such as biotin or thyroxine, as well as enzymes such as hydrolases or peroxidases, or a chemiluminescer such as luciferin, or fluorescent compounds like fluorescein and its derivatives. Alternatively, the probes can be made inherently fluorescent as described in International Application No. WO 93/16094.

Various degrees of stringency of hybridization can be employed. The more stringent the conditions, the greater the complementarity that is required for duplex formation. Stringency can be controlled by temperature, probe concentration, probe length, ionic strength, time, and the like. Preferably, hybridization is conducted under moderate to high stringency conditions by techniques well know in the art, as described, for example in Keller, G. H., M. M. Manak (1987) *DNA Probes*, Stockton Press, New York, N.Y., pp. 169–170, hereby incorporated by reference.

As used herein, moderate to high stringency conditions for hybridization are conditions which achieve the same, or about the same, degree of specificity of hybridization as the conditions employed by the current inventors. An example of high stringency conditions are hybridizing at 68° C. in 5×SSC/5×Denhardt's solution/0.1% SDS, and washing in 0.2×SSC/0.1% SDS at room temperature. An example of conditions of moderate stringency are hybridizing at 68° C. in 5×SSC/5×Denhardt's solution/0.1% SDS and washing at 42° C. in 3×SSC. The parameters of temperature and salt concentration can be varied to achieve the desired level of sequence identity between probe and target nucleic acid. See, e.g., Sambrook et al. (1989) vide infra or Ausubel et al. (1995) *Current Protocols in Molecular Biology*, John Wiley & Sons, NY, N.Y., for further guidance on hybridization conditions.

Specifically, hybridization of immobilized DNA in Southern blots with $^{32}P$-labeled gene specific probes was performed by standard methods (Maniatis et al.) In general, hybridization and subsequent washes were carried out under moderate to high stringency conditions that allowed for detection of target sequences with homology to the exemplified xynA sequences. For double-stranded DNA gene probes, hybridization can be carried out overnight at 20–25° C. below the melting temperature (Tm) of the DNA hybrid in 6×SSPE 5×Denhardt's solution, 0.1% SDS, 0.1 mg/ml denatured DNA. The melting temperature is described by the following formula (Beltz, G. A., Jacobe, T. H., Rickbush, P. T., Chorbas, and F. C. Kafatos [1983] *Methods of Enzymology*, R. Wu, L, Grossman and K Moldave [eds] Academic Press, New York 100:266–285).

$$Tm=81.5° C.+16.6 Log[Na+]+0.41(+G+C)-0.61(\%formamide)-600/length \text{ of duplex in base pairs.}$$

Washes are typically carried out as follows: twice at room temperature for 15 minutes in 1×SSPE, 0.1% SDS (low stringency wash), and once at TM-20° C. for 15 minutes in 0.2×SSPE, 0.1% SDS (moderate stringency wash).

For oligonucleotide probes, hybridization was carried out overnight at 10–20° C. below the melting temperature (Tm) of the hybrid 6×SSPE, 5×Denhardt's solution, 0.1% SDS, 0.1 mg/ml denatured DNA. Tm for oligonucleotide probes was determined by the following formula: TM(° C.)=2 (number T/A base pairs +4(number G/C base pairs) [Suggs, S. V., T. Miyake, E. H., Kawashime, M. J. Johnson, K. Itakura, and R. B. Wallace (1981) *ICB-UCLA Symp. Dev. Biol. Using Purified Genes*, D. D. Brown (ed.), Academic Press, New York, 23:683–693].

Washes were typically carried out as follows: twice at room temperature for 15 minutes 1×SSPE, 0.1% SDS (low stringency wash), and once at the hybridization temperature for 15 minutes in 1×SSPE, 0.1% SDS (moderate stringency wash).

In general, slat and/or temperature can be altered to change stringency. With a labeled DNA fragment >70 or so bases in length, the following conditions can be used: Low, 1 or 2×SSPE, room temperature; Low, 1 or 2×SSPE, 42° C.; Moderate, 0.2× or 1×SSPE, 65° C.; and High, 0.1×SSPE, 65° C.

Duplex formation and stability depend on substantial complementarity between the two strands of a hybrid, and, as noted above, a certain degree of mismatch can be tolerated. Therefore, the probe sequences of the subject invention include mutations (both single and multiple), deletions, insertions of the described sequences, and combinations thereof, wherein said mutations, insertions and deletions permit formation of stable hybrids with the target polynucleotide of interest. Mutations, insertions, and deletions can be produced in a given polynucleotide sequence in many ways, and those methods are known to an ordinarily skilled artisan. Other methods may become known in the future.

Thus, mutational, insertional, and deletional variants of the disclosed nucleotide sequences can be readily prepared by methods which are well known to those skilled in the art. These variants can be used in the same manner as the exemplified primer sequences so long as the variants have substantial sequence homology with the original sequence. As used herein, substantial sequence homology refers to homology which is sufficient to enable the variant polynucleotide to function in the same capacity as the polynucleotide from which the probe was derived. Preferably, this homology is greater than 80%, more preferably, this homology is greater than 85%, even more preferably this homology is greater than 90%, and most preferably, this homology is greater than 95%. The degree of homology or identity needed for the variant to function in its intended capacity depends upon the intended use of the sequence. It is well within the skill of a person trained in this art to make mutational, insertional, and deletional mutations which are equivalent in function or are designed to improve the function of the sequence or otherwise provide a methodological advantage. Methods for confirming promoter activity an xylan- or xylose responsiveness are known in the art.

Polymerase Chain Reaction (PCR) is a repetitive, enzymatic, primed synthesis of a nucleic acid sequence. This procedure is well known and commonly used by those skilled in this art [see Mullis, U.S. Pat. Nos. 4,683,195, 4,683,202, and 4,800,159; Saiki et al. (1985) *Science* 230:1350–1354]. PCR is based on the enzymatic amplification of a DNA fragment of interest that is flanked by two oligonucleotide primers that hybridize to opposite strands of the target sequence. The primers are oriented with the 3' ends pointing towards each other. Repeated cycles of heat denaturation of the template, annealing of the primers to their complementary sequences, and extension of the annealed primers with a DNA polymerase result in the amplification of the segment defined by the 5' ends of the PCR primers. Since the extension product of each primer can serve as a template for the other primer, each cycle essentially doubles the amount of DNA template produced in the previous cycle. This results in the exponential accumulation of the specific target fragment, up to several million-fold in a few hours. By using a thermostable DNA polymerase such as the Taq polymerase, which is isolated from the thermophilic bacterium *Thermus aquaticus*, the amplification process can be completely automated. Other enzymes which can be used are known to those skilled in the art.

It is well known in the art that the polynucleotide sequences of the present invention can be truncated and/or mutated such that certain of the resulting fragments and/or mutants of the original full-length sequence can retain the desired characteristics of the full-length sequence. A wide variety of restriction enzymes which are suitable for generating fragments from larger nucleic acid molecules are well known. In addition, it is well known that Bal31 exonuclease can be conveniently used for time-controlled limited digestion of DNA. See, for example, Maniatis (1982) *Molecular Cloning: A Laboratory Manual*, Cold Spring Harbor Laboratory, New York, pages 135–139, incorporated herein by reference. See also Wei et al. (1983 *J. Biol. Chem.* 258:13006–13512. By use of Bal31 exonuclease (commonly referred to as "erase-a-base" procedures), the ordinarily skilled artisan can remove nucleotides from either or both ends of the subject nucleic acids to generate a wide spectrum of fragments which are functionally equivalent to the subject nucleotide sequences. One of ordinary skill in the art can, in this manner, generate hundreds of fragments of controlled, varying lengths from locations all along the original xynA molecule. The ordinarily skilled artisan can routinely test or screen the generated fragments for their characteristics and determine the utility of the fragments as taught herein. It is also well known that the mutant sequences of the full length sequence, or fragments thereof, can be easily produced with site directed mutagenesis. See, for example, Larionov, O. A. and Nikiforov, V. G. (1982) *Genetika* 18(3):349–59; Shortle, D, DiMaio, D., and Nathans, D. (1981)*Annu. Rev. Genet.* 15:265–94; both incorporated herein by reference. The skilled artisan can routinely produce deletion-, insertion-, or substitution-type mutations and identify those resulting mutants which contain the desired characteristics of the full length wild-type sequence, or fragments thereof, i.e., those which retain promoter activity and also provide xylan- or xylose-regulated transcription of downstream sequence.

DNA sequences having at least 90, or at least 95% identity to the recited DNA sequences of SEQ ID NO:1 and functioning to up-regulate expression of an associated heterologous sequence in response to xylan or xylose (and expressing only at low levels when glucose is present) are considered the most preferred equivalents to the sequences of SEQ ID NO:1. Such functional equivalents are included in the definition of a regulated xynA transcription regulatory sequence. Following the teachings herein and using knowledge and techniques well known in the art, the skilled worker will be able to make a large number of operative embodiments having equivalent DNA sequences to those listed herein without the expense of undue experimentation.

As used herein percent sequence identity of two nucleic acids is determined using the algorithm of Karlin and Altschul (1990) Proc. Natl. Acad. Sci. USA 87:2264–2268, modified as in Karlin and Altschul (1993) Proc. Natl. Acad. Sci. USA 90:5873–5877. Such an algorithm is incorporated into the NBLAST and XBLAST programs of Altschul et al. (1990) J. Mol. Biol. 215:402–410. BLAST nucleotide searches are performed with the NBLAST program, score= 100, wordlength=12, to obtain nucleotide sequences with the desired percent sequence identity. To obtain gapped alignments for comparison purposes, Gapped BLAST is used as described in Altschul et al. (1997) Nucl. Acids. Res. 25:3389–3402. When utilizing BLAST and Gapped BLAST programs, the default parameters of the respective programs (NBLAST and XBLAST) are used. See http://www.ncbi.nih.gov.

The xynA promoter and optionally, where secreted protein is desired, signal peptide coding sequence can be used for high yield of foreign protein expression in recombinant Aureobasidium host cells in which it is expressed. Any host cell in which the signal sequence is expressed and processed may be used. Preferred host cells are members of the genus Aureobasidium, especially *A. pullulans*. Filamentous fungi such as Aspergillus, Trichoderma, Penicillium, etc. are also useful host organisms for expression of the DNA of this invention. (Van den Handel, C. et al. (1991) In: Bennett, J. W. and Lasure, L. L. (eds.), *More Gene Manipulations in Fungi*, Academic Press, Inc., New York, 397–428). When the xynA, transcriptional regulatory (promoter) sequence and the sequence encoding the XynA signal peptide are ligated to DNA encoding other proteins expressible in these hosts, the gene products are secreted from these organisms because of the interaction of the signal peptide with the cell's secretory pathway.

In a preferred embodiment, vectors suitable for transformation of the host, preferably *A. pullulans*, with the xynA transcription regulatory sequences and the DNA coding for the XynA signal peptide are operably linked to the coding sequence of a protein of interest expressible in *A. pullulans* or other host cell of interest. Preferably sequences from SEQ ID NO:1 which are 3' to the coding region for the signal peptide are present or other sequences signaling the transcription stop site. The vector is used to transform the host either by integration into the chromosome or otherwise. The host organism is then cultured under conditions allowing expression of the gene and the product recovered from the culture medium. Levels of expression of proteins of interest utilizing the XynA regulated transcription control sequence and with the XynA (or other) signal peptide sequence are surprisingly high.

Proteins are widely used in pharmaceutical, food, chemical and other industries. The production of medically useful protein and peptide through microbial fermentation is possible due to the advances in genetic engineering. Many recombinant pharmaceutical proteins are produced using *Escherichia coli* and *Saccharomyces cerevisiae* [Achstetter and Wolf (1985) *EMBO J*. 41:173–177; Collins (1990) in: T. J. R. Harris (ed.), *Protein Production by Biotechnology*, Elsevier Applied Science, NY, pp.61–77; Das and Shultz (1987) *Biotechnol. Progress* 3:43–48; Hitzeman et al. (1981) *Nature* (London) 293:717–722] as host cells. Unlike *A. pullulans*, which naturally secretes high levels of the xylanase with relative purity, *E. coli, S. cerevisiae* and *Pichia pastoris* do not naturally secrete high levels of proteins into the culture medium. Production of biologically active and structurally authentic proteins and peptides in the culture medium offer many advantages including the likelihood of correct folding and glycosylation, lack of cell disruption, and ease of product purification.

The *A. pullulans* xynA promoter is highly up-regulated by the presence of xylan or xylose in culture medium [Leathers et al. (1984) supra; Leathers et al. (1986) supra; Li et al. (1993) supra; Li and Ljungdahl (1994) supra; and Wymelenberg et al. (1999) supra] when the glucose concentration is less than about 0.02% (w/v). *Pichia pastoris* has been used as a recombinant host for protein production, but the alcohol oxidase 1 gene (AOX1) is up-regulated by a critical concentration of dissolved oxygen in the culture medium. It has been documented that supplying inducing levels of dissolved oxygen is difficult, particularly in production-scale fermentations where demand for oxygen is high due to high cell density [Romanos et al. (1992) *Yeast* 8:423–488]. The *A. pullulans* xynA promoter is tightly regulated by inexpensive carbon sources, and the highly efficient protein secretion capacity of *A. pullulans* has allowed the development of an efficient protein expression and secretion system in this organism.

Southern hybridization analysis using two different restriction enzymes revealed that EcoRI and HindIII digestion of the *A. pullulans* genomic DNA gave a hybridizing band of about 2.0 kb. The fact that the cloned xynA-coding region lacks both EcoRI and HindIII recognition sequences indicated that the xynA gene is within the 2.0-kb genomic fragment. A genomic DNA library was constructed using λ as a vector, and three positive λ clones were isolated during screening using a 300-bp DNA probe. Positive λ DNA samples (20 ug) were digested with the two enzymes and separated by preparative agarose gel electrophoresis. DNA size standards were electrophoresed under the same conditions. After ethidium bromide staining, the 2.0 kb band was excised and DNA fragments in the agarose gel was extracted and purified. The fragments were ligated into EcoRI and HindIII digested pUC18, and the ligation solution was used for *E. coli* transformation. Plasmids with the 2.0-kb fragment insert were sequenced (Table 1). The plasmid pUC18 harboring the 2.0-kb fragment has been named pRK1. The insert consists of 1965 bp, with the xynA open reading frame extending from nucleotides 727 to 1472. That leaves 726 and 493 bp upstream and downstream of the coding sequence, respectively. There is a TATA box 42 bp upstream of the open reading frame and which TATA box is followed by a C+T region, both of which are believed to be involved in transcription initiation.

Plasmid pUC18 was used as the initial vector for the construction of a protein expression and secretion system for *A. pullulans*. PCR amplifications allowed the generation of specific regions and the addition or removal of certain restriction endonuclease cleavage sites to the regions. The xynA 5 region spanning the xynA promoter and translation start sequences as well as the secretion signal sequence were inserted into pUC18, resulting in pXL5'. To produce proteins of interest intracellularly, a plasmid pXLIN5' lacking the signal peptide sequence and the intron was created. The HindIII site at the beginning of the xynA locus in pRK1 was eliminated while HindIII, BanII, SacII and XbaI downstream of the signal sequence in pXL5' and downstream of the start codon in the case of pXLIN5' were added. The next step involved inserting the xynA 3' sequence into pXL5' and pXLIN5'. More restriction sites, including XbaI, BanI, AvaI, KpnI, and SmaI, were engineered into the downstream region. These plasmids were named pXL53 and pXLIN53, respectively. The $hyg^R$ gene [Staben et al. (1989) *Fungal Genet. Newsl*. 36:79–81] was cloned into the NheI site of the xynA 3' region, 117 bp downstream of the xynA stop codon to allow for selection of transformed cells. The plasmids after insertion of the $hyg^R$ were named pXL1.1 and pXLIN1.1. Because only 117 bp of xynA downstream sequence might not have been sufficient to function as a terminator, the yeast iso-1-cytochrome c terminator (Tcyc) was inserted between the xynA stop codon and the *A. nidulans* TrpC promoter, which resulted in pXL2.1 (FIG. 1B) and pXLIN2.1. Restriction maps of the multiple cloning site regions of pXL2.1 and pXLIN2.1 are shown in Table 3.

The coding region of *E. coli* GUS gene was amplified and inserted into both pXL2.1 and pXLIN2.1. After transformation of *A. pullulans*, 4 primary transformants grown on hygromycin B-containing solid medium were picked from each transformation and purified after multiple rounds of growth on selection and non-selection media. The cells were subsequently inoculated on either glucose or xylose solid media in the presence of 50 µl/plate X-G1cU, a chromogenic substrate of the GUS marker. There was no difference in terms of size and color between colonies transformed with the two plasmids. No difference was found for the transformants growing on either xylose or glucose media. Blue color started to appear 30 hr after inoculation for pXL2.1/GUS and after 50 hr for pXLIN2.1/GUS transformants around colonies on xylose plates. There was no blue color around colonies grown on glucose plates under the same conditions. Negative control colonies transformed with pXL2.1 did not give blue color, even after 96 hr of incubation on xylose medium. These data indicate that the GUS gene expressed under the control of the xynA 5' upstream regulatory sequence was regulated by carbon sources, and that the XynA signal peptide facilitated the secretion of the heterologous GUS enzyme. The low levels of blue color outside of the pXLIN1.1/GUS at a late stage of incubation may be due to release of intracellular enzymes, hydrolyzed product or both. Intracellularly active GUS protein in *A. pullulans* was expressed under the control of a constitutive promoter [Li et al. (1997) *Fungal Genetics Newsletter* 44:29–32]. Clear haloes of about 0.5 cm around well-separated pXL2.1/ LICA were visualized when grown on D-xylose medium for 40 hr but not on glucose medium. Haloes were not detected until about 72 hr of incubation around pXLIN2.1/LICA transformants on xylose medium. These data verify that the transcription of the xynA promoter in the fungus is tightly regulated by carbon sources and that a signal peptide is required for efficient secretion of the proteins from the fungus.

Monoclonal or polyclonal antibodies, preferably monoclonal, specifically reacting with a protein of interest can be made by methods well known in the art. See, e.g., Harlow and Lane (1988) *Antibodies: A Laboratory Manual*, Cold Spring Harbor Laboratories; Goding (1986) *Monoclonal Antibodies: Principles and Practice*, 2d ed., Academic Press, New York; and Ausubel et al. (1993) *Current Protocols in Molecular Biology*, Wiley Interscience/Greene Publishing, New York, N.Y.

Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al. (1989) *Molecular Cloning*, Second Edition, Cold Spring Harbor Laboratory, Plainview, N.Y.; Maniatis et al. (1982) *Molecular Cloning*, Cold Spring Harbor Laboratory, Plainview, N.Y.; Wu (ed.) (1993) *Meth. Enzymol.* 218, Part I; Wu (ed.) (1979) *Meth. Enzymol.* 68; Wu et al. (eds.) (1983) *Meth. Enzymol.* 100 and 101; Grossman and Moldave (eds.) *Meth. Enzymol.* 65; Miller (ed.) (1972) *Experiments in Molecular Genetics*, Cold Spring Harbor Laboratory, Cold Spring Harbor, N.Y.; Old and Primrose (1981) *Principles of Gene Manipulation*, University of California Press, Berkeley; Schleif and Wensink (1982) *Practical Methods in Molecular Biology*; Glover (ed.) (1985) *DNA Cloning* Vol. I and II, IRL Press, Oxford, UK; Hames and Higgins (eds.) (1985) *Nucleic Acid Hybridization*, IRL Press, Oxford, UK; Setlow and Hollaender (1979) *Genetic Engineering: Principles and Methods*, Vols. 1–4, Plenum Press, New York; and Ausubel et al. (1992) *Current Protocols in Molecular Biology*, Greene/Wiley, New York, N.Y. Abbreviations and nomenclature, where employed, are deemed standard in the field and commonly used in professional journals such as those cited herein.

All references cited in the present application are incorporated by reference herein to the extent that there is no inconsistency with the present disclosure.

The following examples are provided for illustrative purposes, and are not intended to limit the scope of the invention as claimed herein. Any variations in the exemplified articles which occur to the skilled artisan are intended to fall within the scope of the present invention.

EXAMPLES

Example 1

Cloning and Sequencing the A. pullulans xynA Locus

*A. pullulans* Y-2311-1 (USDA Culture Collection Center, Peoria, Ill.) was plated from frozen glycerol stock and grown as single colonies on solid potato dextrose medium (Difco, BD Biosciences, Franklin Lakes, N.J.) at 28° C. A single colony was inoculated into a 250 ml shaking flask containing 50 ml YM medium [Leathers et al. (1984) supra]. Glucose (1.0%, w/v) was used as carbon source in YM medium. The flask was shaken at 200 rpm at 28° C. Cells were harvested after the $OD_{600}$ reached 1.5 and subjected to DNA extraction and purification according to Black et al. [(1989) *Biochem. J.* 263:973–976]. Purity of the genomic DNA was analyzed using 0.8% (w/v) agarose gel electrophoresis and ethidium bromide staining according to Sambrook et al. [(1989) supra]. A genomic library was constructed using the lambda FIX II system (Stratagene, San Diego, Calif.). DNA hybridization probe synthesis and screening of the genomic library were carried out as described [Li and Ljungdahl (1994) supra]. A 300-bp cDNA sequence was amplified by polymerase chain reactions (PCR) using pCE4 [Li and Ljungdahl (1996) supra] as a template and the APXF and APXR oligonucleotides as primers and labeled with digoxigenin (Roche Molecular Biochemicals, Indianapolis, Ind.) during the amplification. Primers APXF and APXR, which correspond in sequence to nucleotides 239–260 and 517–537 of Genbank Accession No. U10298 [Li and Ljungdahl (1994) supra], are synthesized. Hybridizing plaques were identified after screening about $10^6$ plaques. The primary plaques were purified with secondary screening. Lambda DNA of the purified phages was isolated after infecting *E. coli* XL-Blue cells using a Qiagen λ Purification System (Qiagen, Valencia, Calif.). Restriction analysis of the purified λ DNA samples was done using EcoRI, HindIII XbaI, KpnI, XhoI, pairwise and combinations of these enzymes. Digested DNA samples were size-separated by electrophoresis on a 1.0% agarose gel and subjected to Southern analysis using the 300-bp amplimer probe. Identified bands were cut out of a gel after another λ sample was separated, and the DNA bands visualized with ethidium bromide staining. pUC18 plasmid (Clontech Laboratories, Palo Alto, Calif.) (5 μg in 50 μl) was digested using both EcoRI and HindIII, and the large fragment was purified using the DNA Purification Kit (Qiagen). Ligation of the EcoRI/HindIII digested DNA fragment and pUC18 was done by using a T4 ligase (New England Biolabs, Beverly, Mass.) and the ligation solution was used to transform *E. coli* XL-Blue (Stratagene). Colonies grown on LB medium containing 50 μg/ml ampicillin were picked and inoculated into liquid LB medium (5 ml). After overnight shaking of the cultures at 200 rpm at 37° C., plasmid DNAs were purified and analyzed by EcoRI and HindIII digestion and agarose gel electrophoresis. Plasmid inserts of the correct sizes were subjected to nucleotide sequencing on an Automatic Dyedeoxyl Terminator System (Applied Biosystems, Inc., Foster City, Calif.) using pUC18 universal and xynA specific primers designed according to the previously published cDNA sequence [Li and Ljungdahl (1994) supra]. Sequence data were analyzed using the Genetics Computer Group software package (University of Wisconsin Biotechnology center, Madison, Wis.) and the VAX/VMS system of the BioScience Computing Resource, University of Georgia, Athens, Ga.

The cDNA cloning and sequence of xynA are also described in U.S. Pat. No. 5,591,619, which is incorporated by reference herein.

Example 2

Construction of Expression Vectors

Figure 1B:
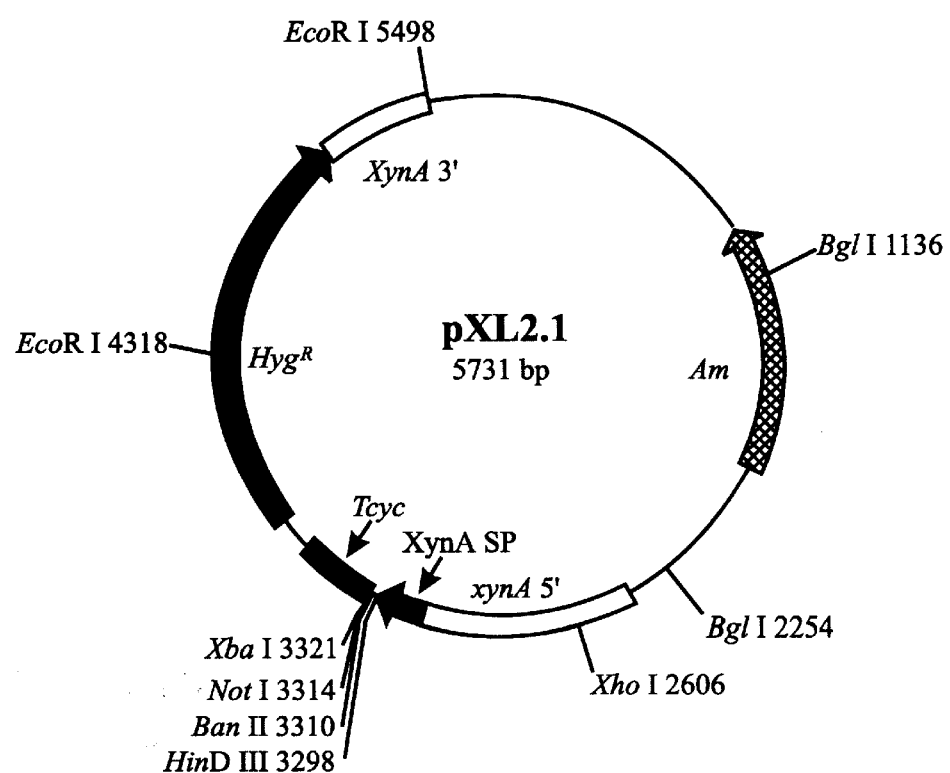

Oligonucleotides PUC-Hind5' and SIG-MCS or IN-MCS were used to amplify either nucleotides 1-891 (5' long region) or 1-733 (5' short region) (Table 1). The 5' long region contains the promoter, ribosome binding site and translation start signals, and the signal peptide coding sequences whereas the 5' short region is the same as the 5' long region except that the signal peptide coding sequence is missing. There was a HindIII site in the PUC-Hind5' and IN-MCS regions (Table 2) but it was inactivated by changing T to A at nucleotide 6. Restriction sites HindIII, BanII, SacII, and XbaI are downstream of nucleotide 891 in PUC-MCS and 733 in IN-MCS. After amplification by PCR using Pfu polymerase (Stratagene) and using PUC-Hind5' with SIG-MCS and IN-MCS as primers and *A. pullulans* genomic DNA as template, the PCR amplification product was purified using a PCR purification kit (Qiagen) and digested with XbaI. pUC18 DNA was first digested with HindIII, and the 5' overhangs were filled in with a Klenow polymerase Fill-In kit (Stratagene). After purification with a Qiagen DNA purification kit, the linearized plasmid was digested with XbaI. Both PCR products and the digested plasmid were subjected to 1.0% agarose gel electrophoresis, and the DNA bands were visualized by ethidium bromide staining, excised from the gel, and purified. Ligation of HindIII-XbaI cut pUC18 with the similarly digested PCR products and transformation of *E. coli* XL-Blue cells were done as described [Sambrook et al. (1989) supra]. Plasmids were purified from the transformed *E. coli* cells after overnight growth in liquid LB medium containing 50 $\mu$g/ml ampicillin. The successful cloning of the PCR product into pUC18 was verified by restriction endonuclease digestion analysis and sequencing. The plasmids were named pXL5' and pXLIN5' with PUC-MCS and IN-MCS, respectively. To clone the 3' untranslated sequences of xynA into PXL5' and pXLIN5', MCS-2 and PUC-ECO3' as primers and genomic DNA as template were used during PCR. The amplified products, pXL5', pXLIN5' were each digested with EcoRI and XbaI and purified. Ligation of the linearized pXL5' or pXLIN5' with xynA 3' region and transformation of *E. coli* XL-Blue were done as described above. The resulted plasmids were named pXL53 and pXLIN53. Finally, the DNA region coding for the *E. coli* hygromycin B resistant gene (hyg$^R$) operably linked to the *Aspergillus nidulans* TrpC promoter was amplified by PCR using HygF and HygR and pCB1636 (Fungal Genetics Stock Center, University of Kansas Medical Center, Kansas City, Kans.) as template. The amplified 1.5-kb fragment, pXL53, and pXLIN53 were each digested with NheI and purified. Again, they were ligated and used to transform *E. coli* XL-Blue. Plasmids purified from transformed cells were analyzed to verify the presence of the 1.5-kb hyg$^R$ insert. The plasmids harboring the xynA 5' and 3' regions as well as hyg$^R$ were named pXL1.1 and pXLIN1.1, as illustrated in FIG. 1A. Plasmid pXLIN1.1 was identical to pXL1.1 except that it lacked the XynA signal peptide coding sequence. To insert a yeast terminator between the stop codon of xynA and the *A. nidulans* trpC promoter, PCR was used to amplify the 260-bp terminator of the yeast iso-1-cytochrome c (CYC1) [Tcyc, Zaret and Sherman (1982) *Cell* 28:563–573] using oligonucleotides TCYCF and TCYCR as primers and pYES2 (Invitrogen Corporation, San Diego, Calif.) as a template, respectively. Recognition sites for XbaI and SmaI were added to TCYCF and TCYCR. Amplified PCR product was purified and digested by XbaI and SmaI and then ligated with XbaI and SmaI digested pXL1.1 and pXLIN1.1. Transformation, purification of plasmids, and restriction analysis were carried out as described above. After all functional fragments were assembled into pUC18, both strands were sequenced to verify the lack of any unwanted point mutation or frame shifting. The plasmids were named pXL2.1 (FIG. 1B) and pXLIN2.1. As in pXL1.1 and pXLIN1.1, the only difference between pXL2.1 and pXLIN2.1 is that pXLIN2.1 lacks the XynA signal peptide coding sequence.

PCR amplification was used to generate genes coding for two heterologous enzymes, the *E coli* β-glucuronidase [GUS, Gallagher (1992) *GUS Protocols, Using GUS Gene as a Reporter of Gene Expression*, Academic Press, San Diego, Calif.] and the lichenase A [LICA, Chen et al. (1997) *J. Bacteriol.* 179:6028–6034] of an anaerobic fungus, Orpinomyces strain PC-2. For the amplification of the GUS, PCR was set for 30 cycles with each cycle of 45 second denaturing at 95° C., 120 second extension at 72° C., and 45 second annealing at 45° C. on a Thermocycler using primers GUSF and GUSR, Pfu polymerase, and plasmid pB101 (Clontech) as template. The reactions generated a DNA molecule corresponding in sequence to nucleotides 7141 to 8911 in pB101 coding for amino acid 2 to 589 of the GUS. HindIII and XbaI sites were added to GUSF and GUSR to facilitate cloning of the fragment into pXL2.1 and pXLIN2.1. In the case of LICA, a DNA fragment was amplified with Pfu polymerase using LICAF and LICAR as primers and pLIC6 [Chen et al. (1997) supra] as template. PCR conditions were set for 30 cycles with each cycle of 45 second denaturing at 95° C., 120 second extension at 72° C., and 45 second annealing at 45° C. The amplified product coded for the mature (secreted) polypeptide (amino acids 30 to 245) of the lichenase and contained SacI and XbaI sites at 5' and 3' ends, respectively for facilitating the cloning of the product into pXL2.1 and pXIN2.1.

Both amplified PCR products and vectors were digested with restriction enzymes and purified after separation on agarose gels. Transformation of *E. coli* XL-Blue and identification of plasmids that contain inserts of the correct sizes were carried out as described above. Plasmids with correctly sized inserts were sequenced on an automatic sequencer using both universal and sequence-specific primers to confirm the lack of unwanted point mutation or frame shifting. Plasmid preparations were obtained using the Qiagen Miniprep DNA purification kit. Transformation of *A. pullulans* cells were performed in a manner similar to the procedure developed for the fungus *Ustilago maydis* [Wang et al. (1988) *Proc. NatL. Acad. Sci. USA* 85:865–869]. Briefly, A single colony of *A. pullulans* grown on solid YM medium was inoculated into a 250 ml Erlenmeyer flask containing 50 ml defined dextrose medium. The flask was shaken at 28° C. until the OD$_{600}$ reached 1.0 (approximately 14 hr). Cells were harvested by centrifugation (1500×g for 15 min) at 4° C. and resuspended in 20 ml of a freshly prepared solution of 5 mM EDTA, pH 8.0/25 mM 2-mercaptoethanol. After gently shaking at room temperature for 20 min, cells were collected by centrifugation (1500×g for 15 min) and then resuspended in 10 ml buffer 1 (1 M sorbitol/50 mM sodium citrate, pH 5.8). A filter-sterilized solution of lysing enzymes containing cellulase, protease and chitinase from *Trichoderma harzianum* (Novozym 234, Sigma Chemical Co., St. Louis, Mo.) 100 mg/ml in Buffer 1) was added to a final concentration of 0.25% (v/v). After 5 min at room temperature, spheroplasts were collected by centrifugation (140×g, 8 min) in a refrigerated table-top centrifuge. The pellet was washed twice in 10 ml buffer 2 (25 mM CaCl$_2$/25 mM Tris-HCl, pH 7.5/1.0 M sorbitol). Spheroplasts were resuspended (7×10$^8$) in buffer 2 (1.0–5.0 ml). The transformation procedure was the same except that only one layer of medium (Holliday's complete medium plus 1 M sorbitol and 2.0% agar) containing 100 $\mu$g/ml hygromycin B (Roche, Indianapolis, Ind.) was used for selection of transformants. Plates were incubated at 28° C. for 3–4 days. Yeast colonies were picked and streaked to fresh hygromycin-containing plates. Subsequently, colonies were transferred to Holliday's complete medium plates without hygromycin B and incubated at 28° C. for 3 days. Finally, the transformants were transferred back to hygromycin-containing solid medium, and only those growing after two days were further analyzed for heterologous enzyme production.

Solid medium for activity detection was Holliday's complete medium containing 1.0% (w/v) of either dextrose or xylose. To detect *A. pullulans* colonies that produce GUS activity, 50 μl of GUS substrate X-G1cU (5-bromo-4-chloro-3-indolyl β-D-glucuronide, Gold Biotechnology, St. Louis, Mo.) was spread on surface of Holliday's complete medium plates (100 mm) using a glass loop. Plates were left on a sterilized surface in a Laminar Flow hood with lid open for at least 15 min before inoculation. Activity was indicated by the presence of blue color. The substrate for lichenase detection was AZO-Barley glucan (Megazyme International Ltd., Wicklow, Ireland). The liquid substrate (5.0%, v/v) was added before autoclaving the medium. The production of lichenase resulted in the formation of clear haloes around the colonies on this medium.

TABLE 1

Nucleotide and deduced amino acid sequences of the *Aureobasidium pullulans* xynA locus. The TATA box is underlined. See also SEQ ID NOs:1 and 2.

```
AAGCTTGTTGAACAAGCCTTGATTTCCGCACAATAGTGCGTTTCAGGCGGAGCCGAGGTC    60
AGGCTCGGGCGCTCGAATTGTGGAGTGCTGAAGACATCTACTACTCATTTATGAGAATGC   120
TTCATCTCTTCCGCGTTCTCGCAAGGATTTATATTAAGCCAGGAGGTCAGCTAATCTGTA   180
TCTGCATACCCGCATATCACTCGAGTGGGTACACGACAGAATCTCGAACTGGCGAATTGC   240
GAAAGCATCGCGTGGTGTTCCTGCAGCGAACAAATAGAGATAAAGTTACACACCACGACC   300
CGACCCCACATCCTTTATAGCGGCTAAGGTGTAAGTTTCACGCCTGCATGGAAGCATGCA   360
CCAGACGATATAGAGTATATGCTACAATATAAGCTCTCGGCCGTACAACGTTCTTCGTAT   420
AGCCATACTTCGAGTATACCAATGACACGTCCGGATAAAAGAGTCAGAGCCATCCAAACA   480
CAGCATTTCGCGTGGAGCATATCCAAGCGAGGTGTCGTGCTTGTCTCGTCACACTTTAAT   540
CTGCTTCGCATTCGATTTCAGGCGAGCAAGGATATCCCAGATTCAGATCTAACAAAATC   600
ACGGCTAAACGATGCCTGGATAGGATATATAAGGACTACCACCTTCCCTCCCATCAGCAA   660
CTCATTCTAGCACATTCATTCAAATCCATTCACATCCATTCAAACAATACTTCCAACTCT   720
CTTCAACATGAAGTTCTTCGCCACCATTGCTGCTCTCGTTGTGGGAGCTGTTGCTGCCCC   780
           M  K  F  F  A  T  I  A  A  L  V  V  G  A  V  A  A  P
AGTCGCAGAGGCTGAGGCTGAGGCCAGCAGCCCCATGCTGGTACGATCTCTTCGATGAAC   840
 V  A  E  A  E  A  E  A  S  S  P  M  L
CATTCTATTCGAGACCATCTTGCTGATCAAACACAATAGATCGAACGTGCCGGTCCCGGT   900
                                            I  E  R  A  G  P  G
GGCATCAACTACGTCCAGAACTACAACGGCAACCTGGGCCAGTTCACCTACAATGAGAAC   960
 G  I  N  Y  V  Q  N  Y  N  G  N  L  G  Q  F  T  Y  N  E  N
GCTGGTACCTACTCCATGTACTGGAACAACGGTGTCAATGGCGACTTCGTCGTTGGTCTC  1020
 A  G  T  Y  S  M  Y  W  N  N  G  V  N  G  D  F  V  V  G  L
GGTTGGTCAACCGGTGCTGCCCGCTCCATCACCTACTCTTCCAACTACCAGGCCAGCGGC  1080
 G  W  S  T  G  A  A  R  S  I  T  Y  S  S  N  Y  Q  A  S  G
GGTTCTTACCTGTCCGTCTACGGCTGGATCAACAGCCCCCAGGCTGAGTACTACATTGTC  1160
 G  S  Y  L  S  V  Y  G  W  I  N  S  P  Q  A  E  Y  Y  I  V
GAGTCTTACGGCTCGTACAACCCTTGCGGCGCCGGTCAGTCCGGTGTCACTCAGCTCGGC  1200
 E  S  Y  G  S  Y  N  P  C  G  A  G  Q  S  G  V  T  Q  L  G
ACCGTCTGCAGCGATGGCGCTACCTACACCGTCTACACCGACACTCGTACCAACCAGCCC  1260
 T  V  C  S  D  G  A  T  Y  T  V  Y  T  D  T  R  T  N  Q  P
TCCATCACTGGTACTTCTACCTTCAAGCAGTACTGGTCTGTCCGCCAGACTAAGCGTACT  1320
 S  I  T  G  T  S  T  F  K  Q  Y  W  S  V  R  Q  T  K  R  T
TCCGGCACGGTCACCACTGGCAACCACTTTGCTTACTGGGCCAAGTACGGCTTTGGCAAC  1380
 S  G  T  V  T  T  G  N  H  F  A  Y  W  A  K  Y  G  F  G  N
TCTTACAACTTCCAGGTCATGCCTGTCGAGGCTTTCTCTGGCACTGGTAGCGCCAGTGTC  1460
 S  Y  N  F  Q  V  M  P  V  E  A  F  S  G  T  G  S  A  S  V
ACCGTCTCTTAAATGTCGGAACAAGTGGCTGAATTTGGATGTTGGAAAGGAGGTTGTTTG  1520
 T  V  S  *
GGATGCGGATGAAACGCTGATGAAGATATGATGTTGATCTGGTTGTGTCCATTTATGCTA  1580
GCTTGTCATTCGTTAGCACAAAGTAAATGTCAGACACCTTGCTACTACCATATGCTCTCC  1640
ATGCCCTATGAATTTCACTTTTCTGTTCAGTTGAGGGTTTCGGAATTTCGGCCCAGATCA  1700
ATGCATAGGGCAGAAAAATCTGGTGATCTTACTGCCGCAAGTTGGCAGAATTTTCCTAGC  1760
TCAAGGCCAGACTCGATCGTCAAGCTGGCCTGACGTCGTCAACTAGATGAATTATAGTAC  1820
CCTTCAGCCCAGAAAAATGGTAGTCTCGCGATCAGACGTCTTCAGACATTCGAACATGAC  1880
ATGAATATCTACGTCAGGACATACTGAATAAATGGTGTTCGAGTAGATCAGCCTCACGAG  1940
TCCGAGCCATAGGAATCCAGAATTC                                    1965
```

TABLE 2

| | Oligonucleotide Names, Sequences and Sequence Identifiers |
|---|---|
| APXF | ACTACGTCCAGAACTACAACG (SEQ ID NO:3) |
| APXR | ACACTCAGCTCGGCACCGTCT (SEQ ID NO:4) |
| HygF1 | GTA<u>GCTAGC</u>AGTCGACAGAAGATGATAT (SEQ ID NO:5) |
| | (NheI site underlined) |
| HygR1 | CTA<u>GCTAGC</u>GGTCGGCATCTACTCTATT (SEQ ID NO:6) |
| | (NheI site underlined) |
| PUC-Hind5' | CCCAAGCTAGTTGAACAAGCCTTG (SEQ ID NO:7) |
| SIG-MCS | ACC<u>TCTAGA</u>GCGGCCGCGGAGCTCC<u>AAAGCTT</u>GGCACGTTCGATCTATTGTG (SEQ ID NO:8) |
| | (XbaI and HindIII sites underlined) |

TABLE 2-continued

Oligonucleotide Names, Sequences and Sequence Identifiers

| | |
|---|---|
| IN-MCS | ACCTCTAGAGCGGCCGCGGAGCTCCAAAGCTTCTTCATGTTGAAGAGAGTTGG (SEQ ID NO:9) |
| PUC-ECO3' | GG<u>AATTC</u>TGGATTCCTATGGC (SEQ ID NO:10) |
| | (EcoRI site underlined) |
| MCS-2 | GC<u>TCTAGA</u>GGTACCCGGGTAAATGTCGGAACAAGTGG (SEQ ID NO:11) |
| | (XbaI site underlined) |
| GUSF | CCC<u>AAGCTT</u>TTACGTCCTGTAGAAACCCCA (SEQ ID NO:12) |
| | (HindIII site underlined) |
| GUSR | GC<u>TCTAGA</u>TTATGCCAGTCCAGCGTTTTTGCA (SEQ ID NO:13) |
| | (XbaI site underlined) |
| LICAF | TTTG<u>GAGCTC</u>CGGTACTGCTTGGAATGGTAGT (SEQ ID NO:14) |
| | (SacI site underlined) |
| LICAR | CC<u>TCTAGA</u>GTTAGTTTCTTGGTGCATCATAAGA (SEQ ID NO:15) |
| | (XbaI site underlined) |
| TCYCF | CG<u>TCTAGA</u>GGTACCGGGCCGCATCATGTAATTAG (SEQ ID NO:16) |
| | (XbaI site underlined) |
| TCYCR | TA<u>CCCCGGG</u>CCGCAAATTAAAGCCTTC (SEQ ID NO:17) |
| | (SmaI site underlined) |

TABLE 3

Nucleotide and possible coded amino acid sequences around
the multiple cloning sites in pXL2.1 and pXLIN2.1.
The low case letters represent an intron sequence.

pXL2.1
```
       I   E   R   A   K   L   W   S   S   A   A   A   L   G   V   P   G   R   I   M   *          (SEQ ID NO:18)
acaatagATCGAACGTGCCAAGCTTTGGAGCTCCGCGGCCGCTCTAGAGGTACCGGGCCGCATCATGTAATTAG                         (SEQ ID NO:19)
               HindIII  BanII   NotI     XbaI
```
pXLIN2.1
```
                   M   K   L   W   S   S   A   A   A   L   G   V   P   G   R   I   M   *          (SEQ ID NO:20)
CTTCCAACTCTCTTCAACATGAAGCTTTGGAGCTCCGCGGCCGCTCTAGAGGTACCGGGCCGCATCATGTAATTAG                       (SEQ ID NO:21)
                      HindIII  BanII   NotI     XbaI
```

We claim:

1. An isolated nucleic acid molecule comprising an *Aureobasidium pullulans* xynA transcriptional regulatory sequence and a heterologous coding sequence, said transcription regulatory sequence being operably linked to said heterologous coding sequence, wherein said transcription regulatory sequence comprises SEQ ID NO:1, nucleotides 278 to 678, or a sequence having at least 90% sequence identity thereto and exhibiting xylan- and xylose-regulated expression of the heterologous coding sequence.

2. The isolated nucleic acid molecule of claim 1, wherein said transcription regulatory sequence is as set forth in SEQ ID NO:1, nucleotides 178 to 678, or a sequence having at least 90% sequence identity thereto and exhibiting xylan- and xylose-regulated expression of the heterologous coding sequence.

3. The isolated nucleic acid molecule of claim 1, wherein said transcription regulatory sequence is as set forth in SEQ ID NO:1, nucleotides 78 to 678, or a sequence having at least 90% sequence identity thereto and exhibiting xylan- and xylose-regulated expression of the heterologous coding sequence.

4. The isolated nucleic acid molecule of claim 1, wherein said transcription regulatory sequence is as set forth in SEQ ID NO:1, nucleotides 1 to 678, or a sequence having at least 90% sequence identity thereto and exhibiting xylan- and xylose-regulated expression of the heterologous coding sequence.

5. The isolated nucleic acid molecule of claim 1, further comprising a signal peptide-encoding sequence.

6. The isolated nucleic acid molecule of claim 5, wherein said encoded signal peptide has the amino acid sequence set forth in SEQ ID NO:2, amino acids 1 to 34.

7. The isolated nucleic acid molecule of claim 5, wherein said signal peptide-encoding sequence is the sequence set forth in SEQ ID NO:1, nucleotides 728 to 820, operably linked to nucleotides 881 to 889.

8. A recombinant host cell comprising the isolated nucleic acid molecule of claim 1.

9. The recombinant host cell of claim 8, wherein said transcription regulatory sequence is as set forth in SEQ ID NO:1, nucleotides 178 to 678.

10. The recombinant host cell of claim 8, wherein said transcription regulatory sequence is as set forth in SEQ ID NO:1, nucleotides 78 to 678.

11. The recombinant host cell of claim 8, wherein said transcription regulatory sequence is as set forth in SEQ ID NO:1, nucleotides 1 to 678.

12. The recombinant host cell of claim 8, wherein said nucleic acid molecule further comprises a signal peptide-encoding sequence.

13. The recombinant host cell of claim 12, wherein the encoded signal peptide has the amino acid sequence given in SEQ ID NO:2, amino acids 1 to 34.

14. The recombinant host cell of claim 13, wherein the nucleotide sequence encoding said signal peptide is as given in SEQ ID NO:1, nucleotides 728 to 889.

15. The recombinant host cell of claim 14, wherein the nucleotide sequence encoding said signal peptide is as given in SEQ ID NO:1, nucleotides 728 to 820, operably linked to and immediately upstream of the nucleotide sequence as set forth in SEQ ID NO:1, nucleotides 881 to 889.

16. A method for the production of a heterologous protein in *Aureobasidium pullulans*, said method comprising the steps of:
   (a) up-regulating expression of a sequence encoding heterologous protein by adding xylan or xylose to a medium in which a recombinant *Aureobasidium pullulans* cell comprising the isolated nucleic acid molecule of claim 1 is cultured, wherein said medium contains glucose at a concentration less than 0.02% (w/v) and wherein a xynA transcription regulatory sequence is operably linked to the sequence encoding the heterologous protein, whereby the heterologous protein is expressed.

17. The method of claim 16 further comprising the step of recovering the expressed heterologous protein.

18. A kit for expression of a protein of interest, comprising of:

(a) a vector comprising an *Aureobasidium pullulans* xynA transcription regulatory sequence, wherein said transcriptional regulatory sequence comprises SEQ ID NO:1, nucleotides 278 to 678, or a sequence having at least 90% sequence identity thereto and exhibiting xylan- and xylose-regulated expression of the heterologous coding sequence, (b) a culture of host cells to be transformed, and (c) instructions for use of said vector to transform said host cells.

19. The kit of claim 18, wherein the culture of host cells is *Aureobasidium pullulans* and wherein the vector replicates in *Aureobasidium pullulans*.

20. The kit of claims 19, wherein said transcription regulatory sequence is as set forth in SEQ ID NO:1, nucleotides 178 to 678, or a sequence having at least 90% sequence identity thereto and exhibiting xylan- and xylose-regulated expression of the heterologous coding sequence.

21. The kit of claim 19, wherein said transcription regulatory sequence is as set forth in SEQ ID NO:1, nucleotides 78 to 678, or a sequence having at least 90% sequence identity thereto and exhibiting xylan- and xylose-regulated expression of the heterologous coding sequence.

22. The kit of claim 19, wherein said transcription regulatory sequence is as set forth in SEQ ID NO:1, nucleotides 1 to 678, or a sequence having at least 90% sequence identity thereto and exhibiting xylan- and xylose-regulated expression of the heterologous coding sequence.

23. The kit of claim 19, wherein said transcription regulatory sequence is selected from the group consisting of nucleotides 1 to 678 of SEQ ID NO:1, nucleotides 78 to 678 of SEQ ID NO:1, nucleotides 178 to 678 of SEQ ID NO:1, and nucleotides 178 to 678 of SEQ ID NO:1.

24. The kit of claim 23, wherein said vector further comprises a signal peptide-encoding sequence.

25. The kit of claim 24 wherein said encoded signal peptide has the amino acid set forth in SEQ ID NO:2, amino acids 1 to 34.

26. The kit of claim 23, wherein the culture of host cell is *Aureobasidium pullulans* Y-2371-1.

27. An isolated nucleic acid molecule comprising an *Aureobasidium pullulans* xynA transcriptional regulatory sequence and a heterologous coding sequence, said transcription regulatory sequence being operably linked to said heterologous coding sequence, wherein said transcription regulatory sequence comprises SEQ ID NO:1, nucleotides 478 to 678, or a sequence having at least 90% sequence identity thereto and exhibiting xylan- and xylose-regulated expression of the heterologous coding sequence.

28. The isolated nucleic acid molecule of claim 27, wherein said transcription regulatory sequence is as set forth in SEQ ID NO:1, nucleotides 378 to 678, or a sequence having at least 90% sequence identity thereto and exhibiting xylan- and xylose-regulated expression of the heterologous coding sequence.

29. The isolated nucleic acid molecule of claim 27 wherein said nucleic acid molecule further comprises a signal peptide-encoding sequence.

30. The isolated nucleic acid molecule of claim 29, wherein the encoded signal peptide has the amino acid sequence given in SEQ ID NO:2, amino acids 1 to 34.

31. A recombinant host cell comprising the isolated nucleic acid molecule of claim 27.

32. The recombinant host cell of claim 31 wherein said nucleic acid molecule further comprises a signal peptide-encoding sequence.

33. The recombinant host cell of claim 32 wherein said encoded signal peptide has the amino acid sequence given in amino acids 1 to 34 of SEQ ID NO:2.

34. A method for the production of a heterologous protein in *Aureobasidium pullulans*, said method comprising the steps of:

(a) up-regulating expression of a sequence encoding heterologous protein by adding xylan or xylose to a medium in which a recombinant *Aureobasidium pullulans* cell comprising the isolated nucleic acid molecule of claim 27 is cultured, wherein said medium contains glucose at a concentration less than 0.02% (w/v) and wherein a xynA transcription regulatory sequence is operably linked to the sequence encoding the heterologous protein, whereby the heterologous protein is expressed.

* * * * *